United States Patent
Nie et al.

(10) Patent No.: US 9,926,253 B2
(45) Date of Patent: Mar. 27, 2018

(54) METHOD FOR CATALYTIC DEHYDRATION OF GLYCEROL TO ACROLEIN

(71) Applicant: ZHEJIANG UNIVERSITY OF TECHNOLOGY, Zhejiang (CN)

(72) Inventors: Yong Nie, Zhejiang (CN); Qinglong Xie, Zhejiang (CN); Ruchao Gong, Zhejiang (CN); Ying Duan, Zhejiang (CN); Shanshan Li, Zhejiang (CN); Yang Liu, Zhejiang (CN); Xiaojiang Liang, Zhejiang (CN); Zhenyu Wu, Zhejiang (CN); Meizhen Lu, Zhejiang (CN); Fengwen Yu, Zhejiang (CN); Jianbing Ji, Zhejiang (CN)

(73) Assignee: ZHEJIANG UNIVERSITY OF TECHNOLOGY, Zhejiang (CN)

( * ) Notice: Subject to any disclaimer, the term of this patent is extended or adjusted under 35 U.S.C. 154(b) by 0 days.

(21) Appl. No.: 15/605,915

(22) Filed: May 25, 2017

(65) Prior Publication Data
US 2017/0342008 A1    Nov. 30, 2017

(30) Foreign Application Priority Data
May 30, 2016 (CN) .......................... 2016 1 0366224

(51) Int. Cl.
| C07C 45/52 | (2006.01) |
| B01J 23/00 | (2006.01) |
| B01J 27/00 | (2006.01) |
| C07C 45/00 | (2006.01) |
| B01J 23/30 | (2006.01) |
| B01J 27/188 | (2006.01) |
| B01J 35/00 | (2006.01) |

(52) U.S. Cl.
CPC ............ *C07C 45/002* (2013.01); *B01J 23/30* (2013.01); *B01J 27/188* (2013.01); *B01J 35/002* (2013.01)

(58) Field of Classification Search
CPC ........ C07C 45/002; B01J 23/30; B01J 27/188
USPC ......................................... 568/486
See application file for complete search history.

(56) References Cited

U.S. PATENT DOCUMENTS

| 5,387,720 | A  * | 2/1995 | Neher .................... C07C 45/52 568/449 |
| 7,396,962 | B1 * | 7/2008 | Dubois ................... C07C 45/52 568/485 |
| 7,790,934 | B2 * | 9/2010 | Redlingshofer ......... B01J 23/30 568/41 |
| 8,604,234 | B2 * | 12/2013 | Paul ....................... B01J 27/188 558/315 |
| 9,079,841 | B2 * | 7/2015 | Lauriol-Garbey ..... B01J 21/063 |

* cited by examiner

*Primary Examiner* — Sikarl A Witherspoon
(74) *Attorney, Agent, or Firm* — JCIPRNET

(57) ABSTRACT

A novel method for catalytic dehydration of glycerol to acrolein is provided. A fixed bed reactor is used, which is placed in a microwave unit. The feedstock is introduced into the fixed bed reactor after being preheated and gasified. Continuous glycerol dehydration occurs in the presence of a microwave-absorbing catalyst in the fixed bed reactor to form acrolein. The microwave-absorbing catalyst is composed of an active component loaded on a core-shell structure which consists of microwave absorbent coated by an oxide. The uniformity of microwave heating can reduce the formation of hot spot during the reaction and hence improve the catalyst stability. The process and operation is simple, and the unit can steadily run for a long time.

10 Claims, 1 Drawing Sheet

METHOD FOR CATALYTIC DEHYDRATION OF GLYCEROL TO ACROLEIN

CROSS REFERENCE TO RELATED APPLICATIONS

The present application claims the priority benefit of Chinese Patent Application No. 201610366224.3 filed on May 30, 2016. The entirety of the above-mentioned patent application is hereby incorporated by reference herein and made a part of this specification.

TECHNICAL FIELD

The present invention relates to a novel method for catalytic dehydration of glycerol to acrolein, and particularly, to a method for continuously producing acrolein in the presence of a microwave-absorbing catalyst by using glycerol as raw material and microwave as heat provider.

BACKGROUND

Biodiesel is a clean renewable energy source, with glycerol being a main by-product in biodiesel production process. Effective utilization of glycerol can reduce the production cost of biodiesel and hence improve the development of biodiesel industry. Glycerol can be used as raw material to produce many valuable chemicals, among which production of acrolein is a promising route. Acrolein is an important chemical feedstock, which can be used to produce 1,3-propanediol, acrylic acid, methionine, pyridine, methyl pyridine, etc.

Currently acrolein is commercially produced mainly using the method of propylene oxidation. However, producing acrolein using glycerol as raw material is more promising in terms of cost and renewability. Research on glycerol dehydration to acrolein started about 100 years ago and has attracted much attention for about 20 years due to the development of biodiesel industry. However, the research on acrolein production from glycerol dehydration is still in a lab-scale study stage, with fast catalyst deactivation resulting from uneven temperature distribution being the main obstacle. The reported methods to improve the catalyst stability are basically catalyst modification and co-feeding with oxygen. Few studies on device improvement were found.

SUMMARY

This invention intends to overcome the issues of heating uniformity and catalyst stability existing in current technology of glycerol dehydration to acrolein. The invention provides a novel method for catalytic dehydration of glycerol to acrolein. The method has advantages of low energy consumption, high product yield, good catalyst stability, low coking, and ease of coke removal.

Preferably, glycerol used as the raw material is introduced into a fixed bed reactor after being preheated and gasified in a preheater. Continuous glycerol dehydration to acrolein occurs in the presence of a microwave-absorbing catalyst in the fixed bed reactor under microwaves generated by a microwave generator.

Preferably, the microwave-absorbing catalyst is denoted as $A-M_xO_y@MA$ in which A, represents an active component of the microwave-absorbing catalyst, $M_xO_y$ represents a coating material, MA represents a microwave absorbent. The microwave absorbent is coated by the coating material to form a catalyst support of the microwave-absorbing catalyst, denoted as $M_xO_y@MA$.

Preferably, the glycerol used is in an aqueous solution with concentration of 10-60 wt %. The glycerol is preheated and gasified at a temperature of 200-300° C., and the glycerol is dehydrated at a temperature of 250-350° C.

Preferably, the active component of the microwave-absorbing catalyst could be any one of metal oxide, heteropoly acid, phosphate, or sulfate, with a loading amount (weight ratio of A to $M_xO_y@MA$) of 4-20 wt %. The coating material is oxide, with a coating amount (weight ratio of $M_xO_y$ to $M_xO_y@MA$) of 25-75 wt %. The microwave absorbent could be any one of silicon carbide, activated carbon, graphite, or single crystal silicon.

Preferably, the oxide used as the coating material could be zirconium oxide, aluminum oxide, silicon dioxide or titanium oxide.

Preferably, the fixed bed reactor is connected with an inlet and an outlet, with a catalyst bed placed at a center of the fixed bed reactor. The fixed bed reactor is made of a material that is microwave transmitting and high temperature resistance.

Preferably, the material that is microwave transmitting and high temperature resistance could be glass or ceramics.

Preferably, the microwave generator is connected with a temperature controller, a paperless recorder, and an infrared sensor successively. The infrared sensor is used to accurately measure a temperature of a catalyst bed in the fixed bed reactor, and a measured data is transmitted to the temperature controller through the paperless recorder. When the temperature reaches a set point, the microwave unit is controlled to be on or off by the temperature controller.

Preferably, the process for preparing the microwave-absorbing catalyst is as follows:

1) To prepare the catalyst support $M_xO_y@MA$, the microwave absorbent is first dispersed in a water bath at 60° C. and being mixed with a dispersant to form a solution. A precursor of the coating material is then added into the solution, followed by addition of ammonia and keeping a pH of the solution stable, the added precursor is hydrolyzed so as to form the coating material that is coated onto the microwave absorbent. After completion of reaction, the solution is filtered, washed, dried, and calcined to form the catalyst support of the microwave-absorbing catalyst $M_xO_y@MA$. The above-mentioned precursor of the coating material could be compounds containing zirconium, aluminum, silicon, or titanium, which can be hydrolyzed to form the coating material such as zirconium oxide, aluminum oxide, silicon dioxide or titanium oxide.

2) The active component or a precursor of the active component is dissolved in water, and then added to the solution of the catalyst support of the microwave-absorbing catalyst prepared in step 1) for impregnation. Subsequently, after complete impregnation, the impregnated solution is dried, calcined, squashed, and sieved to obtain the microwave-absorbing catalyst.

Preferably, the dispersant could be sodium metasilicate or tetramethyl ammonium hydroxide.

Preferably, the microwave unit comprises the following parts: microwave generator, temperature controller, infrared sensor, feed inlet, product outlet, and fixed bed reactor. Microwaves generated by the microwave generator are absorbed by the catalyst in the fixed bed reactor, and hence the fixed bed reactor is heated. Temperature is measured by the infrared sensor, with the signal transmitted to the temperature controller. The microwave generator is then controlled to be on or off by the feedback signal of temperature controller. The process could be on continuous operation.

Compared with conventional techniques, the present invention has the following beneficial effects:

1) Compared with conventional electric heating, the temperature distribution of the catalyst bed is more even when using the microwave heating, hence, reducing the coking on catalyst and improving the catalyst stability.

2) Microwave heating has advantages when applied to catalyst regeneration. Microwave has advantages of rapid and uniform heating, small thermal inertia, and ease of control. Coke can be rapidly heated and removed during catalyst regeneration, with hot spot avoided. Consequently, in-situ activation of catalyst is realized and the time for coke removal is greatly reduced. The cost for catalyst regeneration is then reduced, and the production capacity and benefit are increased.

3) In the present invention, acrolein is continuously produced in the presence of the microwave-absorbing catalyst by using glycerol as raw material and microwave as heating unit. The process has advantages of low energy consumption, high product yield, good catalyst stability, low coking, and ease of coke removal, and consequently, the technique is suitable for popularization and application.

Figure 1:
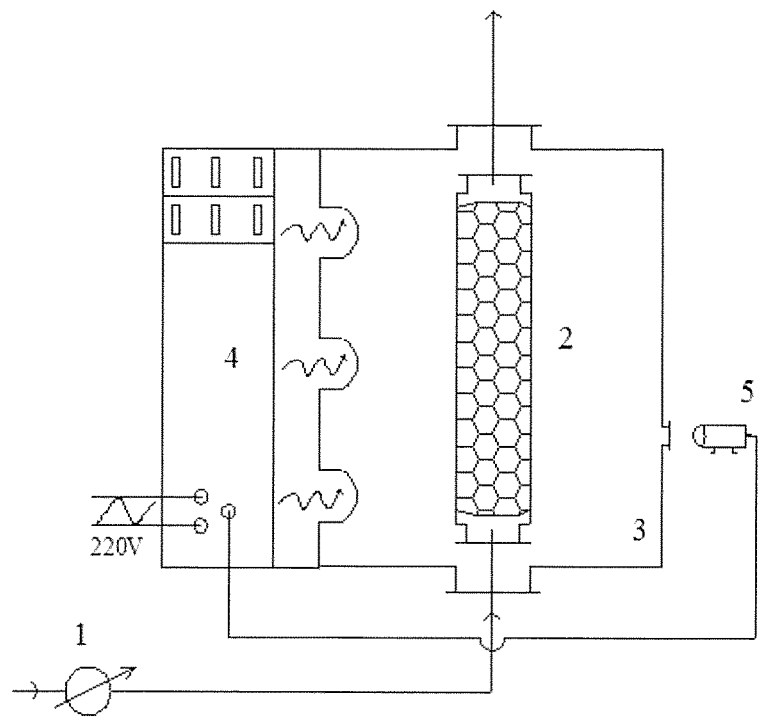
FIG. 1 shows a schematic diagram of the reaction unit in the present invention.

In the Figures, the labels each represents the following: 1: preheater; 2: fixed bed reactor; 3: microwave generator; 4: temperature controller; 5: infrared sensor.

DESCRIPTION OF THE EMBODIMENTS

Reference will now be made in detail to the present preferred embodiments of the invention, examples of which are illustrated in the accompanying drawings. However, the invention is not limited the embodiments shown below.

Embodiment 1: Preparation of Microwave-Absorbing Catalyst $WO_3$—$ZrO_2$@SiC

1) Preparation of Coated Catalyst Support $ZrO_2$@SiC with a $ZrO_2$ Coating Amount of 37.5 wt %:

Ten grams of silicon carbide (SiC) was dissolved in 300 mL of deionized water, followed by addition of sodium metasilicate as a dispersant, the mixture was stirred in a water bath at 60° C. to form a solution. The pH of the dispersion solution was adjusted to 9-10. Zirconium oxychloride solution (16 g $ZrOCl_2.8H_2O$ dissolved in 100 mL deionized water) was then slowly added into the SiC dispersion solution, followed by dropwise addition of ammonia solution (9.4 g of ammonia dissolved in 220 mL deionized water), and the pH was kept stable. After the reaction, the solution was aged for 0.5 hours at the same temperature, and the solution was filtered, washed by 200 mL deionized water for three times, dried at 110° C., and calcined at 550° C. for 2.5 hours to obtain the catalyst support $ZrO_2$@SiC.

2) Loading active component $WO_3$ (tungsten trioxide) with a $WO_3$ loading amount of 8.0 wt %:

Four grams of ammonium metatungstate was dissolved in 70 mL deionized water, and then the solution was added to 40 g of the $ZrO_2$@SiC (prepared in step 1) under stirring for impregnation to form a fluid suspension Meanwhile, the solution was heated using an infrared lamp for 18 hours so as to evaporate water, and then dried at 100° C. and calcined at 600° C. for 6 hours to obtain the microwave-absorbing catalyst $WO_3$—$ZrO_2$@SiC. The catalyst was then squashed and sieved to particles of 10-20 mesh.

Embodiment 2: Preparation of Microwave-Absorbing Catalyst HPW-$Al_2O_3$@AC

1) Preparation of Coated Catalyst Support $Al_2O_3$@AC with $Al_2O_3$ Coating Amount of 37.5 wt %:

Ten grams of activated carbon (AC) was dissolved in 300 mL of deionized water, followed by addition of sodium metasilicate as the dispersant, the mixture was stirred in a water bath at 60° C. to form a solution. The pH of the dispersion solution was adjusted to 8-9. Aluminum nitrate solution (44 g $Al(NO_3)_3.9H_2O$ dissolved in 150 mL deionized water) was then slowly added into the AC dispersion solution, followed by dropwise addition of ammonia solution (25 g of ammonia dissolved in 250 mL deionized water) and the pH was kept stable. After the reaction, the solution was aged for 0.5 hours at the same temperature and another 12 hours at room temperature, and the solution was filtered, washed by 200 mL deionized water for three times, dried at 110° C., and calcined at 550° C. for 2.5 hours to obtain the catalyst support $Al_2O_3$@AC.

2) Loading active component phosphotungstic acid (HPW) with HPW loading amount of 0 wt %:

Phosphotungstic acid solution (4.5 g HPW dissolved in 70 mL deionized water) was added to 40 g $Al_2O_3$@AC under stirring for impregnation to form a fluid suspension. Meanwhile, the solution was heated using an infrared lamp for 18 hours so as to evaporate water, and then dried at 110° C. for 6 hours to obtain the microwave-absorbing catalyst HPW-$Al_2O_3$@AC. The catalyst was then squashed and sieved to particles of 10-20 mesh.

Embodiment 3: Microwave-Assisted Catalytic Dehydration of Glycerol

The catalyst used in this embodiment is $WO_3$—$ZrO_2$@SiC prepared according to embodiment 1, with $WO_3$ loading amount and $ZrO_2$ coating amount being 8.0 wt % and 37.5 wt %, respectively.

Figure 2:
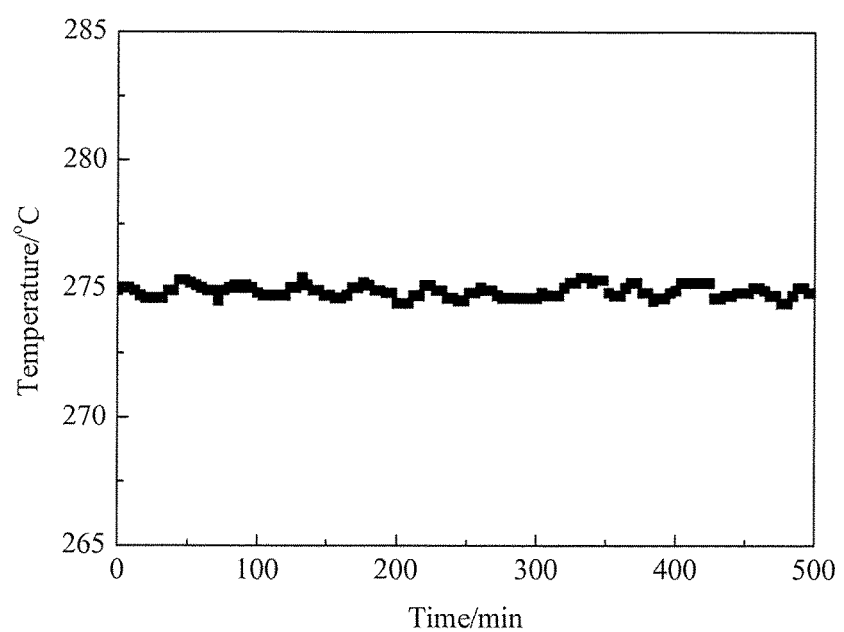
FIG. 2 displays the temperature variation with time during microwave-assisted catalytic dehydration of glycerol for acrolein production.

Nitrogen at a flow rate of 30 mL/min was first introduced into the system, with the preheater (1) and microwave generator (3) turned on for heating (see FIG. 1). When the temperatures of preheater (1) and catalyst bed reaches 220° C. and 275° C., respectively, the temperatures were keep stable for 0.5 hours, and nitrogen introduction was halted thereafter. Glycerol (aqueous solution, 20 wt %), used as a raw material was introduced into the system by a peristaltic pump, with the weight hourly space velocity (WHSV) being 0.2 $h^{-1}$. Reaction results of the embodiment are as follows: during the continuous run for 8 hours, the glycerol conversion is about 100% and acrolein selectivity reaches higher than 70%. The infrared sensor (5) is used to measure the temperature of catalyst in the fixed bed reactor (2), with the signal transmitted to the temperature controller (4). The microwave generator (3) is then controlled to be on or off by the feedback signal of the temperature controller (4). The reaction temperature is ultimately controlled to be 275° C. with the variation of ±1° C. (see FIG. 2).

Embodiment 4: Microwave-Assisted In-Situ Regeneration of Catalyst for Glycerol Dehydration Microwave-assisted catalytic dehydration of glycerol for acrolein production was carried out under the following conditions: the temperatures of preheater (1) and catalyst bed are 220° C. and 275° C., respectively; glycerol (aqueous solution, 20 wt %) was used as the raw material; the weight hourly space velocity (WHSV) of the raw material being 0.2 $h^{-1}$. After continuous run for 100 hours, the glycerol conversion was decreased to about 50%, indicating obvious deactivation of the microwave absorbing catalyst. The feeding was then stopped, and air at a flow rate of 100 mL/min was then introduced into the system and kept stable for 5 min to eliminate the remaining products in the system. Subsequently, microwave generator (3) was turned on, and the temperature of catalyst bed was increased steadily from 275° C. to 500° C. in 1 hour and kept at 500° C. for 2 hours. After the catalyst regeneration, microwave generator (3) is then turned off and the temperature of the catalyst bed is decreased to 275° C. The microwave generator (3) is then turned on again to keep the temperature of the catalyst bed stable at 275° C., and meanwhile, air flow is switched to nitrogen at a flow rate of 30 mL/min. The introduction of nitrogen is kept stable for 0.5 hours to eliminate the remaining air in the system, and nitrogen introduction was halted thereafter. Afterwards, microwave-assisted catalytic dehydration of glycerol was carried out with the same reaction conditions as before. The reaction results are close to those when using fresh catalyst. The glycerol conversion was about 100% and acrolein selectivity reaches higher than 70%.

It can be understood that as for a person of ordinary skill the art, equivalent replacements or changes to the technical scheme or inventive concept in the present invention should be protected according to the claims in the present invention.

What is claimed is:

1. A method for catalytic dehydration of glycerol to acrolein, wherein:
    a glycerol used as raw material is introduced into a fixed bed reactor after being preheated and gasified in a preheater,
    the gasified glycerol is then continuously dehydrated to form acrolein in the presence of a microwave-absorbing catalyst in the fixed bed reactor under microwaves generated by a microwave generator.

2. The method according to claim 1, wherein the microwave-absorbing catalyst is denoted as A-$M_xO_y$@MA, in which:
    A represents an active component of the microwave-absorbing catalyst, $M_xO_y$ represents a coating material, MA represents a microwave absorbent, and the microwave absorbent is coated by the coating material to form a catalyst support of the microwave-absorbing catalyst, denoted as $M_xO_y$@MA.

3. The method according to claim 1, wherein the glycerol used is in an aqueous solution with concentration of 10-60 wt %, and the glycerol is preheated and gasified at a temperature of 200-300° C., and the glycerol is dehydrated at a temperature of 250-350° C.

4. The method according to claim 2, wherein the active component of the microwave-absorbing catalyst is any one of metal oxide, heteropoly acid, phosphate, or sulfate, with a loading amount of 4-20 wt %; the coating material is oxide, with a coating amount of 25-75 wt %; the microwave absorbent is any one of silicon carbide, activated carbon, graphite, or single crystal silicon.

5. The method according to claim 4, wherein the oxide used as the coating material is zirconium oxide, aluminum oxide, silicon dioxide or titanium oxide.

6. The method according to claim 1, wherein the fixed bed reactor is connected with an inlet and an outlet, with a catalyst bed placed at a center of the fixed bed reactor, and the fixed bed reactor is made of a material at is microwave transmitting and high temperature resistance.

7. The method according to claim 6, wherein the material that is microwave transmitting and high temperature resistance is glass or ceramics.

8. The method according to claim 1, wherein the microwave generator is connected with a temperature controller, a paperless recorder, and an infrared sensor (5) successively, the infrared sensor is used to accurately measure a temperature of a catalyst bed in the fixed bed reactor, and a measured data is transmitted to the temperature controller through the paperless recorder; when the temperature reaches a set point, the microwave generator is controlled to be on or off by the temperature controller.

9. The method according to claim 2, wherein a process for preparing the microwave-absorbing catalyst is as follows:
    1) to prepare the catalyst support $M_xO_y$@MA, the microwave absorbent is first dispersed in a water bath at 60° C. and being mixed with a dispersant to form a solution, a precursor of the coating material is then added into the solution, followed by addition of ammonia and keeping a pH of the solution stable, the added precursor is hydrolyzed so as to form the coating material that is coated onto the microwave absorbent, after completion of reaction, the solution is filtered, washed, dried, and calcined to form the catalyst support of the microwave-absorbing catalyst $M_xO_y$@MA, wherein the precursor of the coating material is compounds containing zirconium, aluminum, silicon, or titanium, which can be hydrolyzed to form the coating material such as zirconium oxide, aluminum oxide, silicon dioxide or titanium oxide;
    2) the active component or a precursor of the active component is dissolved in water, and then added to the solution of the catalyst support of the microwave-absorbing catalyst prepared in step 1) for impregnation, after complete impregnation, the impregnated solution is dried, calcined, squashed, and sieved to obtain the microwave-absorbing catalyst.

10. The method according to claim 9, wherein the dispersant is sodium metasilicate or tetramethyl ammonium hydroxide.

* * * * *